US009233237B2

(12) United States Patent
Ludvig et al.

(10) Patent No.: US 9,233,237 B2
(45) Date of Patent: Jan. 12, 2016

(54) APPARATUS AND METHOD FOR PERIODIC FLUID-DELIVERY/FLUID-REMOVAL CYCLES IN THE CRANIAL SUBARACHNOID SPACE TO TREAT CEREBRAL CORTICAL DISORDERS

(75) Inventors: Nandor Ludvig, Richmond Hill, NY (US); Geza Medveczky, Cortlandt Manor, NY (US); Hai M. Tang, Brooklyn, NY (US); Shirn L. Baptiste, New York, NY (US)

(73) Assignee: NEW YORK UNIVERSITY, New York, NY (US)

( * ) Notice: Subject to any disclaimer, the term of this patent is extended or adjusted under 35 U.S.C. 154(b) by 193 days.

(21) Appl. No.: 12/868,890

(22) Filed: Aug. 26, 2010

(65) Prior Publication Data

US 2012/0053506 A1 Mar. 1, 2012

(51) Int. Cl.
*A61M 5/00* (2006.01)
*A61M 27/00* (2006.01)
*A61B 5/0478* (2006.01)
*A61B 5/00* (2006.01)
*A61M 5/142* (2006.01)
*A61M 37/00* (2006.01)

(52) U.S. Cl.
CPC .......... *A61M 27/006* (2013.01); *A61B 5/0478* (2013.01); *A61B 5/4839* (2013.01); *A61B 5/686* (2013.01); *A61B 5/6868* (2013.01); *A61M 5/14276* (2013.01); *A61M 27/002* (2013.01); *A61M 37/00* (2013.01)

(58) Field of Classification Search
CPC .......... A61M 2005/14208; A61M 2202/0464; A61M 2025/0057; A61M 5/14276; A61M 5/1723; A61M 27/006; A61M 27/002; A61M 2210/0693; A61M 2205/3523; A61B 5/0475; A61B 5/4839; A61B 5/686; A61B 5/6868; A61B 5/031
USPC ............................................................ 604/9
See application file for complete search history.

(56) References Cited

U.S. PATENT DOCUMENTS

| 6,497,699 | B1 | 12/2002 | Ludvig et al. | |
|---|---|---|---|---|
| 2003/0004495 | A1* | 1/2003 | Saul | 604/540 |
| 2003/0100857 | A1* | 5/2003 | Pedrazzi et al. | 604/4.01 |
| 2005/0159697 | A1* | 7/2005 | Dextradeur et al. | 604/8 |
| 2006/0020239 | A1* | 1/2006 | Geiger et al. | 604/9 |
| 2007/0060973 | A1* | 3/2007 | Ludvig et al. | 607/45 |
| 2008/0051691 | A1* | 2/2008 | Dragoon et al. | 604/8 |
| 2008/0249458 | A1 | 10/2008 | Yamasaki | |

(Continued)

OTHER PUBLICATIONS

Ludvig et al. "Localized Transmeningeal Muscimol Prevents Neocortical Seizures in Rats and Nonhuman Primates: Therapeutic Implications", Epilepsia vol. 4, No. 50, 2009, pp. 678-693.

(Continued)

*Primary Examiner* — Tatyana Zalukaeva
*Assistant Examiner* — Ariana Zimbouski
(74) *Attorney, Agent, or Firm* — Fay Kaplun & Marcin, LLP

(57) ABSTRACT

An apparatus for treating the brain comprises an implantable fluid exchange device coupled to a control unit to periodically alternate a delivery of a therapeutic agent with a removal of cerebrospinal fluid from a cranial subarachnoid space to prevent local inflammatory host-products from blocking a transmeningeal diffusion of the therapeutic agents into the cerebral cortex and thereby allow an effective treatment of cerebral cortical disorders by the delivery therapeutic agents.

9 Claims, 4 Drawing Sheets

(56) References Cited

U.S. PATENT DOCUMENTS

2009/0131850 A1* 5/2009 Geiger .............................. 604/9
2010/0179518 A1* 7/2010 Ludvig et al. .............. 604/891.1

OTHER PUBLICATIONS

Ludvig et al., "Evolution and Prospects for Intracranial Pharmacotherapy for Refractory Epilepsies: The Subdural Hybrid Neuroprosthesis, Epilepsy Research and Treatment", Article ID 725696, vol. 2010, http://www.hindawi.com/journals/ert/2010/725696.html, pp. 10 sheets.
Collins, "Anticonvulsant Effects of Muscimol", Neurology vol. 6, No. 301980, pp. 575-581.
Del Bigio, "Biological Reactions to Cerebrospinal Fluid Shunt Devices: A Review of the Cellular Pathology", Neurosurgery, vol. 3, No. 42, 1998, pp. 319-326.
Hassenbusch et al., "Stereotactic Injection of DTI-015 into Recurrent Malignant Gliomas: Phase I/II Trial, Neoplasia", vol. 5, No. 1, Jan. 2003, pp. 9-16.
Ludvig et al., "Toward the Development of a Subdural Hybrid Neuroprosthesis for the Treatment of Intractable Focal Epilepsy", Epilepsia 46, Suppl. 8: 270, 2005, 1 sheet.
Ludvig et al. "Histological Evidence for Drug Diffusion Across the Cerebral Meninges into the Underlying Neocortex in Rats", Brain Research 1188, 2008, pp. 228-232.
Ludvig, et al., "Advances in the Application of Technology to Epilepsy: The CIMIT/NIO Epilepsy Innovation Summit", Epilepsy & Behavior 16, 2009, pp. 3-46.
Ludvig et al., "Muscimol-Delivering Subdural Pharmacotherapy Device for the Treatment of Intractable Neocortical Epilepsy: Preliminary Safety and Efficacy Studies in Freely-Behaving Bonnet Macaques", Epilepsia 0, Suppl 0, Abstract submitted to the 2010 Annual Meeting of the American Epilepsy Society, 2010, 3 sheets.
Sawyer et al., "New Methods for Direct Delivery of Chemotherapy Tumors", Yale Journal of Biology and Medicine 79, 2006, pp. 141-152.
Ludvig, "Subarachnoid Pharmacotherapy for Maximizing Recovery after Cortical Ischemic Stroke", NYU Comprehensive Epilepsy Center, NYU, School of Medicine/Langone Medical Center, NY, NY, USA, J Exp Stroke Transl Med, 2010, pp. 13-21.

* cited by examiner

Before subarachnoid Ach delivery 12 min after subarachnoid Ach delivery 2 min after subarachnoid muscimol delivery

APPARATUS AND METHOD FOR PERIODIC FLUID-DELIVERY/FLUID-REMOVAL CYCLES IN THE CRANIAL SUBARACHNOID SPACE TO TREAT CEREBRAL CORTICAL DISORDERS

FIELD OF THE INVENTION

This invention generally relates to the delivery of drugs and other therapeutic agents directly into the brain via intracranially implanted devices, and particularly relates to effective transmeningeal drug and therapeutic agent delivery for the treatment of neurological disorders with focal cerebral cortical pathology.

BACKGROUND

Transmeningeal delivery refers to a treatment modality in which drugs and other therapeutic agents are delivered into a cranial subarachnoid space to allow them to diffuse through the pia mater into an underlying, diseased cerebral cortical area and thereby correct abnormal neural functions in that cortical area. Neurological disorders with focal cerebral cortical pathology include various forms of focal epilepsy, stroke, traumatic brain injury, and tumors. Although drug delivery directly into the subdural/subarachnoid space of the spinal cord ("intrathecal administration") is widely used in clinical practice for pain relief in obstetric anesthesia, as well as in lower abdominal, urogenital, rectal and lower extremity surgical procedures, the subdural/subarachnoid compartment of the brain is currently not utilized for therapeutic purposes, such as for the treatment of cerebral cortical disorders. This is due to a lack of appropriate devices which are both implantable in the subdural/subarachnoid space without causing significant damage to neural tissue and can also perform localized medication delivery for long periods without an eventual clogging or obstruction in their delivery systems rendering them incapable of functioning as intended. Current experimental or clinically used cannulas, catheters or drug-releasing polymers share the same common problem that bedevils their use. This problem is the induction of inflammatory host responses that encapsulate or clog the implant, preventing its ability to maintain constant, or at least sufficient, therapeutic agent delivery with consequent therapeutic effects. The inflammatory host response is mediated by cells, such as mast cells, macrophages, lymphocytes, fibroblasts and other cellular elements, and by molecules, such as various collagen, elastin, proteoglycans, adhesive glycoproteins and other molecules, which, together accumulate and aggregate, forming a fibrous, gelatinous layer over the dorsal surface of the cerebral cortex and its covering pia mater within 2-3 weeks. This layer of newly generated connective tissue forms a lasting barrier to drugs or other medications and therapeutic agents delivered into the subarachnoid space, effectively blocking their transmeningeal influx into the cortical tissue. As a consequence, presently used or experimental needles, cannulas, catheters, or drug-releasing polymers cannot provide treatment for cerebral cortical disorders for periods longer than 2-3 weeks. This forbids their implantation for the treatment of chronic cerebral cortical disorders, the treatment of which requires persistent treatment over a period of several month or years.

SUMMARY OF THE INVENTION

The present invention relates to a system and method for treating cerebral cortical disorders via a fluid exchange device sized and shaped for placement in a space separating the cranial dura and pia maters. The exemplary system of the present invention includes at least one fluid exchange port equipped with a leakage-preventing seal and at least two tubes, wherein one tube is configured to deliver fluid with therapeutic solutes and wherein the other tube is configured to remove cerebrospinal fluid (CSF) with accumulated inflammatory tissue reaction products from the area of the port, thereby preventing clogging of the fluid delivery tube and therefore allowing effective diffusion of the delivered therapeutic solutes into the treated cerebral cortical region.

The present invention also relates to a method for using the aforementioned fluid exchange device effectively by alternating the fluid delivery/fluid removal cycles with intervals that prevent the aggregation of inflammatory products in the fluid exchange ports, provide effective diffusion of the therapeutic solutes into the treated cortex, and keep the treated cortical surface bathed in a physiological mixture of natural and artificial cerebrospinal fluids.

DETAILED DESCRIPTION

Figure 1:
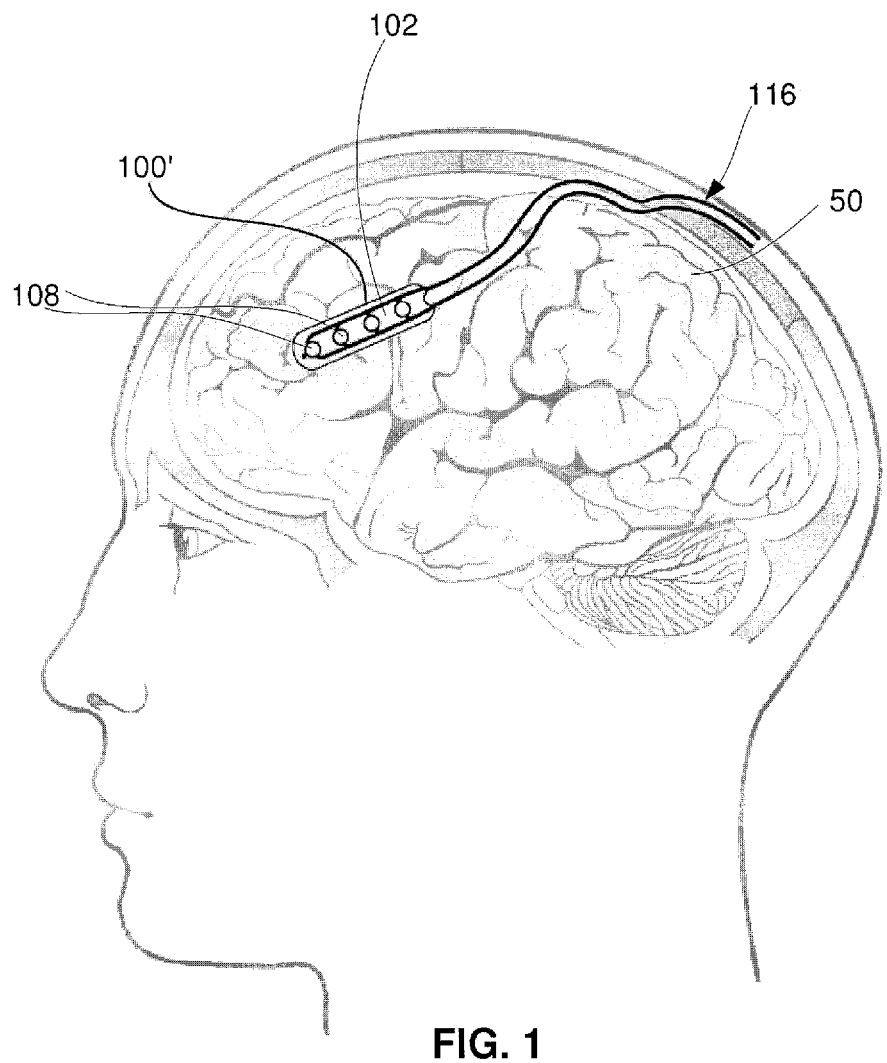
FIG. 1 shows an exemplary embodiment of a subdural/subarachnoid system according to the present invention.

The present invention may be further understood with reference to the following description and the related appended drawings, wherein like elements are provided with the same reference numerals. The present invention describes a system combining pharmacological and electrophysiological instruments for the treatment of brain disorders. A system in accordance with the present invention includes a subdural/subarachnoid therapeutic agent fluid exchange device for implantation in a subdural/subarachnoid space. The device is formed as a thin sheet of flexible biocompatible material suitable for placement in the cranial subdural/subarachnoid space and incorporates multiple sealed fluid-exchange ports, with each port having at least one inlet for local transmeningeal fluid delivery and at least one outlet for local fluid removal. At least some of the inlet and outlet ports further comprise electrode and/or neurochemical sensor contacts to provide feedback on the local cortical effects of the performed fluid deliveries and removals without penetrating into cerebral cortical neural layers. The device of the present invention further comprises a central control unit integrating a mini-pump configured to control a flow of fluids into and out of the subdural/subarachnoid space. The control unit is equipped with miniature subcutaneous ports accessible from the outside the body, for both periodic refilling of the delivery fluids and periodic elimination of the removed fluids therefrom. The mini-pump and control unit are configured to perform both fluid delivery to and fluid removal from the subarachnoid space in an alternating manner to prevent the obstruction of fluid exchange ports of the delivery device while also preventing accumulation and aggregation of local inflammatory and host-response cells and molecules effectively cleansing lumens of the fluid exchange device and creating a condition whereby drugs and other therapeutic agents delivered through the fluid exchange ports can diffuse transmeningally into the underlying cerebral cortical tissue to exert therapeutic action without hindrance. The exemplary embodiment of the present invention produces a long-term stream of fluid delivery and fluid removal cycles in the subdural/subarachnoid space for the treatment of neurological disorders with cerebral cortical pathology, such as focal neocortical epilepsy and some types of stroke, brain injury and brain tumor. It is noted that although the present invention has been described with respect to the treatment of a few neurological conditions, the exemplary systems and methods may also be applied for the treatment of any other neurological abnormalities without deviating from the spirit and scope of the present invention.

Figure 2:
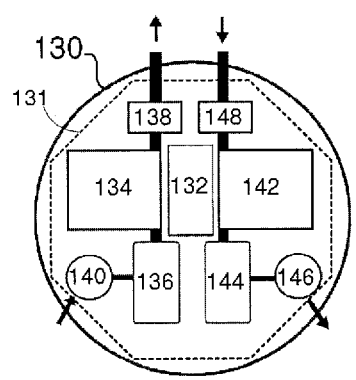
FIG. 2 shows a detailed view of a control unit of the system of FIG. 1.
Figure 3:
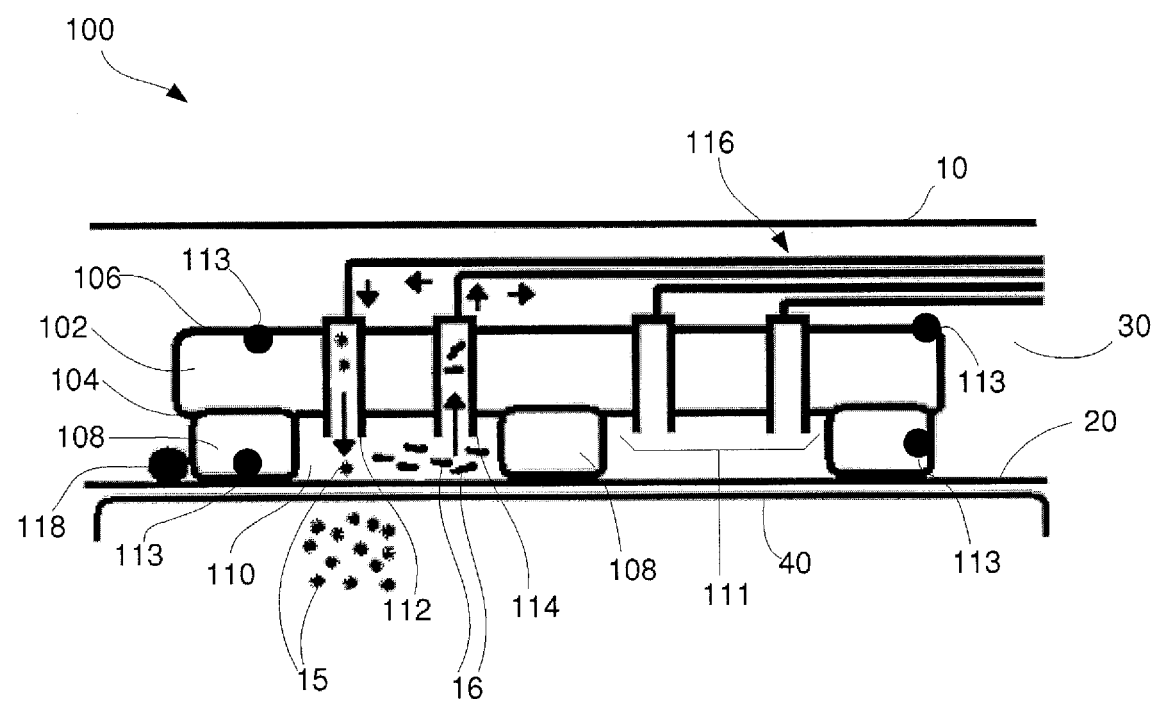
FIG. 3 shows a detailed view of the subdural/subarachnoid strip of FIG. 1.

As shown in FIGS. 1-3, a system 100 according to the present invention comprises a subdural/subarachnoid sheet body 102 implantable into a subdural/subarachnoid space 30 between an arachnoid mater 10 and a pia mater 20 of a cerebral cortex 50. As understood by those skilled in the art the subdural/subarachnoid space 30 is filled with cerebrospinal fluid ("CSF"). The subdural/subarachnoid sheet body 102 is formed as a flexible sheet of bio-compatible material (e.g., silicone) having a thickness smaller than approximately 3 mm. The sheet body 102 comprises a cortical surface 104 configured to be positioned adjacent the pia mater 20 and a dorsal surface 106 configured to be positioned against the arachnoid mater 10 when implanted in the cerebral cortex 50 in an operative configuration. The shape of the sheet 102 of flexible bio-compatible material can be one of a strip and a grid. Furthermore, although the present embodiment is described with a single subdural/subarachnoid sheet body 102 implanted in the cerebral cortex, a single or multiple strips and/or grids may be used in any combination and number, depending on the size and location of the target area such as a cerebral cortical seizure focus, infarct, tumor, area of traumatic injury, as those skilled in the art will understand. Furthermore, the single or plurality of strips and/or grids may be placed either in the subarachnoid space only or in both the subdural and subarachnoid spaces, as those skilled in the art will understand.

A plurality of sealing rings 108 is provided on the cortical surface 104. The sealing rings 108 are configured and dimensioned to contact the pia mater 20 covering a cerebral cortical surface 40 in a manner so that a series of gaps 110 is provided between the pia mater 20 and the cortical surface 104 of the sheet body 102. The gaps 110 are therefore enclosed in a substantially fluid-tight manner so that fluid introduced by the system 100 into each of the gaps 110 is maintained in a target area and is substantially prevented from spilling over to adjacent portions of the cerebral cortex 50 (e.g., non-targeted cortical areas). In the embodiment shown, three rings 108 are provided, creating two separate gaps 110. It is noted however, that any other number of gaps 110 sealing by sealing rings 108 may be integrated within the subdural/subarachnoid system 100 without deviating from the spirit and scope of the present invention.

As shown in FIGS. 1 and 3, a fluid exchange port 111 comprising inlet and outlet tubes 112, 114 opens into each of the gaps 110. The inlet tube 112 delivers a fluid such as a therapeutic drug solution. In an exemplary embodiment, the therapeutic drug solution may be one or more of a drug solution, brain-derived natural molecules, flushing solutions (e.g., saline, etc.), peptides, proteins, genes, cells, etc. The therapeutic drug solution may contain only a single compound or a combination of two or more compounds including anti-inflammatory drugs and other agents that prevent the generation, accumulation and/or aggregation of inflammatory host responses in the cranial subdural/subarachnoid space. The outlet tube 114 is configured to remove fluid such as local cerebrospinal fluid and/or a portion of the delivered therapeutic drug solution from the region of the gap 110. As shown in FIG. 3, one set of inlet and outlet tubes 112, 114 opens into each one of the fluid exchange ports 111 in each of the gaps 110. Proximal portions of these inlet and outlet tubes 112, 114 may be bundled together in a bundle 116 positioned within the sheet body 102 adjacent the dorsal surface 106 thereof, as shown in FIG. 3. The bundle 116 extends out of a cranium of the patient to a central control unit 130, as will be described in greater detail hereinafter. It is noted that although the bundle 116 is depicted in FIG. 1 as a plurality of separated tubes 112, 114, the tubes 112, 114 may be encased in a single tubing arrangement (not shown) or a double tubing arrangement as shown in FIG. 1 for ease of implantation. Furthermore, it is noted that although the present embodiment indicates the opening of one inlet and one outlet tube 112, 114 into each of the gaps 110, the number of either of these tubes may be increased, thus permitting the delivery of two or more therapeutic agents to each fluid exchange port 111 or directing the removed fluids to two or more reservoirs separated from the cranium (e.g., into a pump reservoir and an abdominal space). In another embodiment of the invention, the number, lumen-size and geometric arrangement of the inlet and outlet ports 112, 114 may vary depending on, for example, the characteristics of the targeted cortical tissue. For example, as shown in FIG. 1, a system 100' may be formed with four sealing rings 108 formed as sealing membranes and defining three fluid exchange ports 111 therebetween.

In another exemplary embodiment of the present invention, the system 100 may also comprise EEG electrode contacts or neurochemical sensors 113 to provide feedback for the cortical effects of a delivered therapeutic agent and/or the effects of local fluid removals if these develop. In one embodiment of the invention, the contacts may be EEG electrodes having high frequency field potentials over approximately 100 Hz or, in another embodiment, between approximately 0.1 and 500 Hz. The contacts 113 may be distributed over any portion of the system 100 without deviating from the scope of the present invention. In one exemplary embodiment, the contacts 113 are positioned over predetermined portions of the system 100 adjacent the cortical surface 20. Each of the contacts is connected to a tubing 118 which extends alongside the bundle 116 to a position external to the cranium (e.g., to a position within the central control unit). The contacts 113 may also be configured to monitor levels of local neurotransmitters and metabolites in the brain. As shown in FIG. 3, the wiring of the electrophysiological recording contacts 113 and the bundle 116 for the delivered and removed fluids are led outside of the brain and the cranium to connect to the central control unit 130. It is noted that although FIG. 3 depicts only predetermined positions for contacts 113, any other positions may be employed without deviating from the spirit and scope of the present invention.

The central control unit 130 according to the invention is formed substantially similarly to that of U.S. Pat. No. 6,497, 699 to Ludvig et al. entitled "Hybrid Neuroprosthesis for the Treatment of Brain Disorders" filed on Aug. 9, 2000, the entire disclosure of which is incorporated herein by reference thereto. Specifically, the central control unit 130 comprises a mini-pump 131 and a supporting module 132 consisting of a microcontroller, a bi-directional radiofrequency communication system and a power supply. The mini-pump 131 is configured as a dual mini-pump in order to provide both fluid delivery and fluid removal to and from the subarachnoid sheet body 102. Such a dual mini-pump has been disclosed in greater detail in the publication entitled "Toward the Development of a Subdural Hybrid Neuroprosthesis for the Treatment of Intractable Focal Epilepsy" to Ludvig et al. published in 2005 in Epilepsia 46 (Suppl. 8):270 and the publication entitled "Localized Transmeningeal Muscimol Prevents Neocortical Seizures in Rats and Nonhuman Primates: Therapeutic Implications" to Ludvig et al. published in 2009 in Epilepsia 50:678-693, the entire disclosures of which are incorporated herein by reference thereto. The dual minipump 131 according to the present invention is configured to operate substantially similarly to the previously disclosed mini-pump with the exception of a modification permitting the present mini-pump 131 to perform both fluid delivery and fluid removal in an alternating manner through the sheet body 102. Specifically, the mini-pump 131 has a first pump-compartment 134 directing a drug solution or therapeutic agent solution from a delivery reservoir 136 to each of the inlet tubes 112 of the sheet body 102. A flow of the drug solution to the sheet body 102 may be monitored by a first flow sensor 138 provided in the control unit 130. It is noted that although the first flow sensor 138 is depicted as housed within the control unit 130, the first flow sensor 138 may alternately be disposed at any position between the first pump compartment 134 and the sheet body 102 without deviating from the scope of the invention. The delivery reservoir 136 containing the drug solution may further be connected to a subcutaneous refilling port 140 implanted at a predetermined position within the patient's body. Specifically, the refilling port 140 may be positioned, along with the control unit 130, at a subcutaneous position so that the refilling port 140 may be accessed via a needle or other device inserted through a patient's skin thereinto, as those skilled in the art will understand. Furthermore, in an alternate embodiment of the invention (not shown), the port 140 may be separated from the control unit and connected thereto via tubing.

The mini-pump 131 further comprises a second pump compartment 142 configured to direct fluid movement in a direction opposite that of the first pump compartment 134. Specifically, whereas the first pump compartment directs fluid from the delivery reservoir 136 to the sheet body 102, the second pump compartment 142 applies suction to the outlet tubes 114 to draw fluid away from the sheet body 102 toward a CSF collection reservoir 144 connected thereto. In one exemplary embodiment, the second pump compartment 142 directs removed local CSF from a region adjacent distal openings of each of the outlet tubes 114 into the CSF collection reservoir 144. Movement of CSF and other fluids from the sheet body 102 to the CSF collection reservoir 144 may be monitored by a second flow-sensor 148 positioned along a length of the outlet tube 114. The CSF collection reservoir 144 is further connected to a subcutaneous removal port 146 positioned in a manner similar to the subcutaneous refilling port 140 and permits the permanent removal of collected CSF and other inflammatory products from the body via a needle or other device. The exemplary mini-pump 131 according to the present invention permits the delivery of fluids to and the removal of fluids from the sheet body 102 in a plurality of time intervals, some of which will be discussed in greater detail hereinafter.

It is noted that although the control unit 130 of the present invention is depicted as being implanted at a site remote from the cranium, in an alternate embodiment, the subdural/subarachnoid strip 102 and the control unit 130 may both be configured and dimensioned for implantation at a target subdural/subarachnoid site. In one exemplary embodiment, the subdural/subarachnoid strip 102 and the control unit 130 may be formed as a single unit implantable in the subdural/subarachnoid space. In another embodiment, the control unit 130 may be separated from the subdural/subarachnoid strip 102 and implanted in another portion of the cranium selected by a physician or other user, as those skilled in the art will understand. In one exemplary embodiment, the control unit 130 is implanted at a location separated from the subdural/subarachnoid strip 102 by approximately 30 cm, although any other placement is envisioned without deviating from the spirit and scope of the present invention.

In accordance with an exemplary method according to the present invention, a craniotomy procedure is performed to remove a portion of a skull and provide direct access to a cerebral cortex 50. One or more of the subdural/subarachnoid sheets 102 is then inserted through the craniotomy to rest directly on a target portion of the cerebral cortical surface 40 and held in place by pressure applied thereto by at least the overlying arachnoid mater 10. Once the subdural/subarachnoid sheet bodies 102 have been advanced to a target position in the cerebral cortex 50, a bridge (not shown) formed, for example, of silicone is attached to an unremoved portion of the skull and screwed thereto to maintain a position thereof. As would be understood by those skilled in the art, a location of the bridge may be chosen to lie in proximity to the treatment area comprising the subdural/subarachnoid sheet bodies 102. The tubing 116 extends out of the craniotomy and placed along a predetermined path to the central control unit 130 which may be implanted in a portion of the body separate from the cerebral cortex 50. The craniotomy is then closed.

The exemplary system 100 according to the present invention is configured to induce a sterile inflammatory host reaction to prevent the accumulation and aggregation of inflammatory cells and molecules 16 adjacent to the distal openings of the inlet and outlet ports 112, 114. Unless removed, these inflammatory cells and molecules 16 will obstruct and clog the inlet and outlet ports 112, 114 within a period of approximately two to three weeks after implantation. Once this occurs, and all of the fluid outlet ports 114 have become obstructed along with the subsequent clogging of the upstream fluid inlet tubes 112, the delivery of therapeutic agents 15 through the pia mater and into the diseased cortical tissue is no longer possible. The exemplary system and method according to the present invention provides a solution to this problem by periodically diluting, mobilizing and eliminating the inflammatory tissue reaction cells and molecules 16 that invade the area of the fluid inlet and outlet ports 114. Specifically, dilution is provided by a periodic delivery of a medication or therapeutic agent into each of the gaps 110 through the inlet tubes 112. The delivery of the therapeutic agent not only serves as a treatment for underlying diseased cortical tissue, but also, by the virtue of its solvent water, dilutes the invading, local inflammatory products formed in the region of the gaps 110. The dilution thus helps to prevent the aggregation of inflammatory cells and molecules. Instead, the diluted inflammatory products are mobilized by applying suction to each of the outlet tubes 114. The diluted and mobilized tissue reaction cells and molecules 16 are removed from the outlet tubes 114 via a continued suction, lasting for about 0.2-5 minutes and led into the CSF collection reservoir 144. Removal of the inflammatory cells and molecules 16 permits drugs and other therapeutic agents delivered through the inlet tubes 112 to freely diffuse into the diseased cortical area and exert their therapeutic effects without hindrance.

Figure 4:
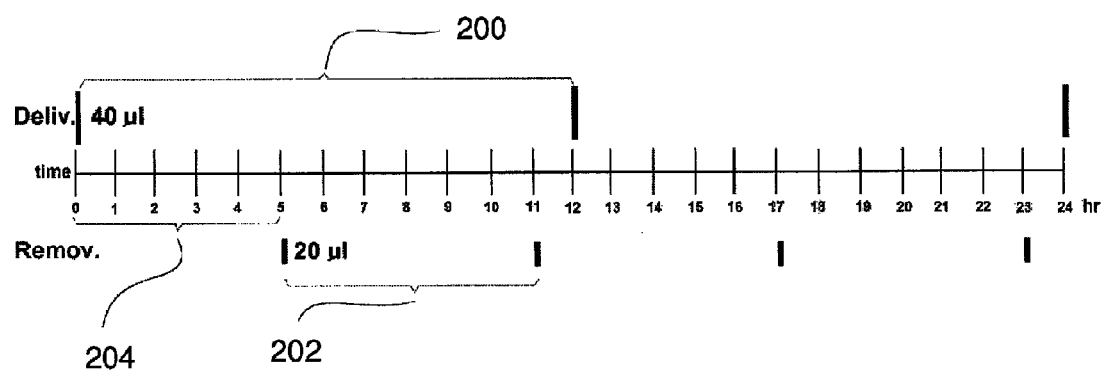
FIG. 4 illustrates a first exemplary method for generating periodic fluid delivery and fluid removal cycles according to the present invention.

FIG. 4 illustrates one exemplary method for periodic subarachnoid fluid delivery and fluid-removal cycles according to the invention. In this method, a predetermined amount (e.g., 40 microliter) of fluid, such as a therapeutic drug solution, is delivered to the subarachnoid space periodically with a 12-hour pause interval 200 between successive deliveries. The 12-hour delivery schedule alternates with fluid removals applied periodically at 6-hour pause intervals 202 between successive removals. As those skilled in the art will understand, a delay period 204 is applied between the first fluid delivery and the first fluid removal so that a temporal relationship between the consecutive delivery and removal cycles can be adjusted. In the exemplary embodiment shown, a volume of approximately 20 microliters of fluid is withdrawn from each of the outlet ports 114 at each removal cycle. It is noted however that the volume of each fluid delivery and removal may be adjusted and tailored to a patient's brain anatomy and physiology, as well as to the conditions of the disease being treated so that each patient may require a specifically tailored subarachnoid therapy schedule. It is therefore respectfully submitted that the volumes and intervals disclosed herein are exemplary only and do not limit the scope of the present invention. Any other volumes and intervals may be employed without deviating from the spirit and scope of the present invention.

Figure 5:
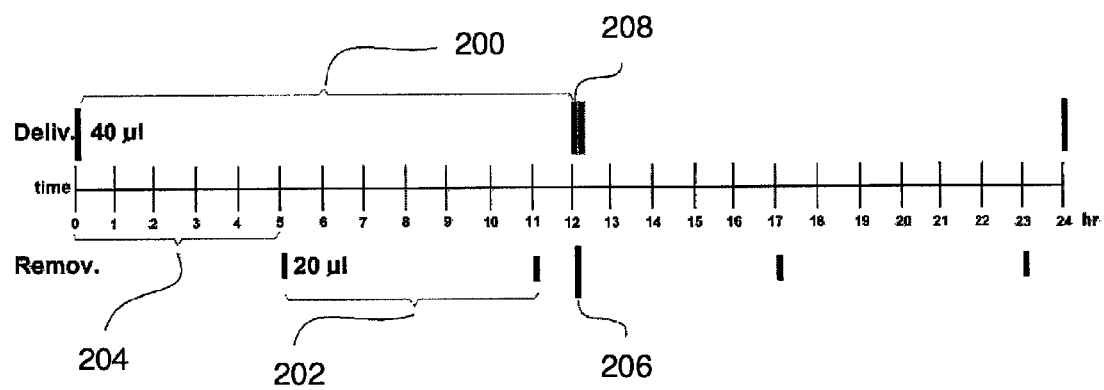
FIG. 5 illustrates a second exemplary method for generating periodic fluid delivery and fluid removal cycles according to the present invention.

FIG. 5 illustrates another method for periodic subarachnoid fluid delivery and fluid removal cycles according to the present invention. The method of FIG. 5 is substantially similar to the method described above with respect to FIG. 4, with the exception of the timing of each of the fluid delivery and removal cycles. Specifically, a first fluid delivery is performed and followed at a first delay 204 of five hours by a first fluid removal. A second fluid delivery is performed at an interval 200 of approximately 12 hours. This delivery is immediately, or with a short delay 206 (e.g., shorter than approximately one minute), followed by a removal of the same amount of fluid. That is, while the periodic fluid removals (e.g., programmed at approximately 6 hour intervals) remove only a portion of the fluid supplied by a previous delivery, the immediate fluid removals remove substantially the same volume of fluids from the gaps 110 as supplied by the fluid delivery. This immediate removal provides a flushing of the gap 110 of the fluid-exchange ports and the lumens of the inlet and outlet tubes 112, 114, respectively, leading to more diluting and more mobilizing effects than that achieved by the method shown in FIG. 4. The immediate flushing is then followed by a subsequent delivery 208 of fluids which then follows the steps disclosed above with respect to FIG. 4. The immediate flushing may be performed at predetermined regular intervals selected by a physician to conform to the needs of a patient. In one embodiment, the flow of fluids into and out of the subdural/subarachnoid space may be controlled by wirelessly programming the control unit 130 to adjust the rate and volume of fluid delivery and withdrawal. Specifically, the control unit 130 may comprise a microcontroller (not shown) configured to be programmable by the physician one of prior to implantation of the device 100 into the patient's body and subsequent to implantation. In another embodiment of the invention, the rates and volumes of fluid delivery and removal may be configured to automatically adjust in response to a detection of predetermined electrophysiological and/or neurochemical signals received from electrodes mounted on the sheet body 102.

Figure 6:
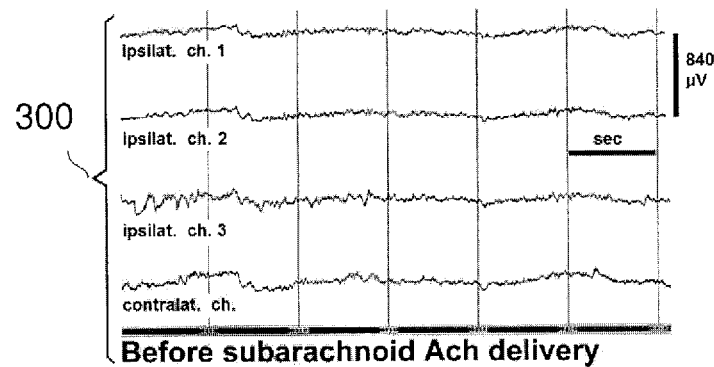
FIG. 6 depicts experimental results obtained in an implanted subdural/subarachnoid sheet body subjected to the periodic fluid delivery and fluid-removal cycles of FIG. 4 prior to the delivery and removal of predetermined fluids.
Figure 7:
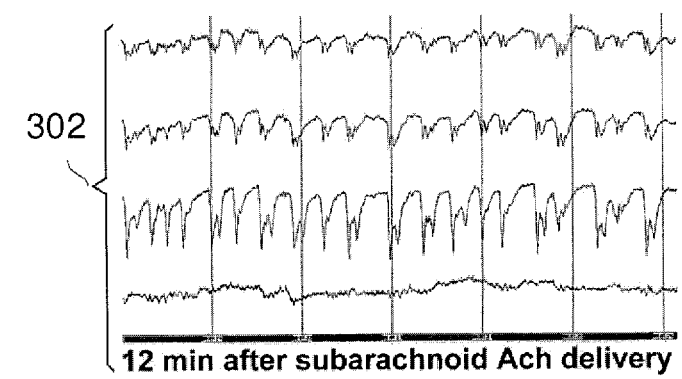
FIG. 7 depicts experimental results obtained in an implanted subdural/subarachnoid sheet body subjected to the periodic fluid delivery and fluid-removal cycles of FIG. 4 recorded 12 minutes after the delivery of a first predetermined fluid.
Figure 8:
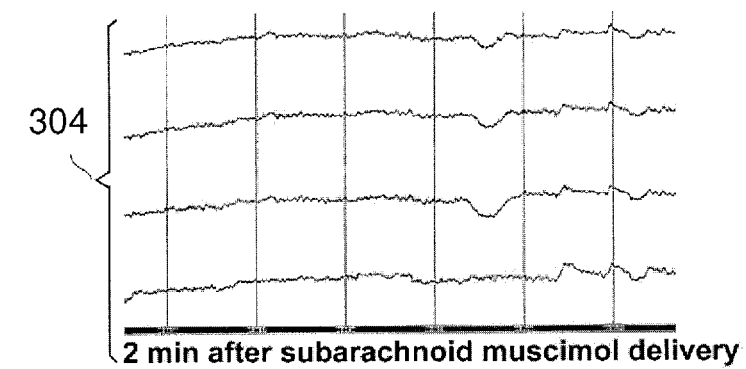
FIG. 8 depicts experimental results obtained in an implanted subdural/subarachnoid sheet body subjected to the periodic fluid delivery and fluid-removal cycles of FIG. 4 recorded 2 minutes after the delivery of a second predetermined fluid.

FIGS. 6-8 depict experimental data obtained in a monkey implanted with the system 100 shown in FIGS. 1-3 and subjected to the periodic fluid delivery and fluid-removal cycles of FIG. 4 over a period of three months. In this experiment, drugs with known pharmacological actions were delivered through the sheet body 102 to test whether the inlet and outlet ports 112, 114 were clogged or obstructed, with the effects of the administered drugs monitored via EEG electrode contacts 113 integrated into the sheet body 102. The experiment was performed in a monkey approximately three months after the implantation of the sheet body 102 over the animal's right frontal cortex and the implantation of the control unit 130. During this post-surgical period, the delivery fluid was saline. On the day of this experiment, the mini-pump was temporarily modified to deliver a seizure-inducing agent (acetylcholine) through the sheet body 102, followed by a delivery of an antiepileptic drug (muscimol) through the same route. Traces 1 to 3 of FIG. 6 represent EEG recordings obtained with the EEG electrodes integrated into the subarachnoid sheet (ipsilateral recording channels 1, 2 and 3). The fourth trace of FIG. 6 was obtained from a subdural/subarachnoid electrode placed, during device implantation, in the left-side frontal cortex (contralateral recording channel). Before drug delivery, the EEG recordings showed normal patterns 300. After delivering acetylcholine through the sheet body 102, characteristic EEG seizure patterns 302 developed in ipsilateral/treatment area channels 1, 2 and 3 but not in a contralateral/non-treated area channel 4, as shown in FIG. 7. When muscimol was subsequently delivered through the inlet and outlet ports 112, 114, the EEG seizure stopped within 2 min, as shown the EEG recordings 304 of FIG. 8. The onset and cessation of the seizure activity exhibits that the subarachnoid inlet and outlet ports 112, 114 were not obstructed or clogged, because both acetylcholine and muscimol delivered to the frontal cortical subarachnoid space was shown to cause clear, localized EEG effects. Examination of the content of the collection reservoir 144 of the mini-pump 131 proved the presence of inflammatory cells and molecules in the removed CSF. In another monkey, not subjected to similar periodic subarachnoid fluid delivery and fluid removal cycles and only to periodic saline deliveries, the inlet and outlet ports 112, 114 and the tubing of the system 100 was clogged approximately three weeks after implantation. Thus, localized drug effects, such as those shown in FIGS. 6-8 could not be obtained unless the tubing was manually cleansed in the anesthetized animal.

Although the present invention is designed ultimately for human use, its applicability should not be limited to use solely on human subjects. For example, the scope of the apparatus and methods of the present invention includes the use of the present invention in animals as a means to test the safety and effectiveness of therapeutic agents on the brain in conjunction with the system of the present invention.

There are many modifications of the present invention which will be apparent to those skilled in the art without departing from the teaching of the present invention. The embodiments disclosed herein are for illustrative purposes only and are not intended to describe the bounds of the present invention which is to be limited only by the scope of the claims appended hereto.

What is claimed is:

1. A method for treating a brain of a subject, comprising:
implanting a fluid exchange device in a subdural or subarachnoid space of the brain, the fluid exchange device comprising a body portion sized and shaped for placement entirely within the subdural or subarachnoid space, an inlet opening extending through the body portion to a first fluid exchange port, and an outlet opening extending through the body portion to the first fluid exchange port;
implanting a fluid delivery/withdrawal device at a location in the subject's body remote from a first target area of the subdural or subarachnoid space, the first fluid delivery/withdrawal device including a delivery lumen coupled to the inlet opening and an outlet lumen coupled to the outlet opening, the fluid delivery/withdrawal device being coupled to a source of a first fluid; and
operating a control unit to administer the first fluid to the first target area via the inlet opening and withdraw fluid from the first target area at predetermined periodic intervals and volumes, wherein the intervals and volumes are selected by the control unit to reduce accumulation of inflammatory host responses in the target area.

2. The method of claim 1, wherein amounts of fluid withdrawn from the first target area correspond to amounts of the first fluid supplied thereto to maintain a desired level of fluid within the first target area.

3. The method of claim 1, wherein the controlling step comprises further determining a first predetermined interval for periodically administering the first fluid to the first target area, and a second predetermined interval for periodically withdrawing fluid from the first target area, wherein the first predetermined interval is longer than the second predetermined interval.

4. The method of claim 3, further comprising the step of wirelessly programming the control unit to adjust the predetermined periodic intervals and volumes.

5. The method of claim 3, wherein the control unit is configured to automatically adjust the predetermined periodic intervals and volumes in response to detection of a predetermined electrophysiological or neurochemical signal.

6. The method of claim 1, wherein fluid is withdrawn from the first target area ten minutes after the first fluid is administered to the first target area, or less than one minute after the first fluid is administered to the first target area.

7. The method of claim 6, wherein a predetermined amount of the first fluid is administered to the first target area immediately after withdrawal of fluid therefrom.

8. The method of claim 1, further comprising the step of refilling a first drug reservoir holding the first fluid via a subcutaneous refilling port to the first drug reservoir.

9. The method of claim 1, further comprising the steps of collecting fluid withdrawn from the first target area in a first collection reservoir, and permanently removing fluid withdrawn from the collection reservoir via a fluid removal subcutaneous port connected thereto.

* * * * *